US006828313B2

(12) United States Patent
Fishbein (10) Patent No.: US 6,828,313 B2
(45) Date of Patent: Dec. 7, 2004

(54) USE OF OXANDROLONE IN THE TREATMENT OF BURNS AND OTHER WOUNDS

(75) Inventor: Don Fishbein, Westfield, NJ (US)

(73) Assignee: Savient Pharmaceuticals, Inc., East Brunswick, NJ (US)

( * ) Notice: Subject to any disclaimer, the term of this patent is extended or adjusted under 35 U.S.C. 154(b) by 0 days.

(21) Appl. No.: 10/011,377

(22) Filed: Oct. 22, 2001

(65) Prior Publication Data

US 2002/0165266 A1 Nov. 7, 2002

Related U.S. Application Data

(63) Continuation of application No. 08/985,734, filed on Dec. 5, 1997, now Pat. No. 6,576,659.
(60) Provisional application No. 60/032,414, filed on Dec. 5, 1996.

(51) Int. Cl.$^7$ .......................... A61K 31/56; A61K 31/58

(52) U.S. Cl. ........................... 514/171; 514/2; 514/175; 514/179; 514/925; 514/928

(58) Field of Search ........................... 514/2, 171, 175, 514/179, 925, 928

(56) References Cited

U.S. PATENT DOCUMENTS

| | | | |
|---|---|---|---|
| 3,128,283 A | | 4/1964 | Pappo et al. |
| 5,461,030 A | | 10/1995 | Lindenbaum |
| 5,532,230 A | * | 7/1996 | Daynes et al. ............... 514/178 |
| 5,872,147 A | | 2/1999 | Bowen |
| 5,922,701 A | * | 7/1999 | Araneo ....................... 514/178 |
| 6,090,799 A | * | 7/2000 | Berger ........................ 514/179 |
| 6,576,659 B1 | | 6/2003 | Fishbein |
| 6,670,351 B1 | | 12/2003 | Berger |
| 2002/0091155 A1 | | 7/2002 | Berger |
| 2003/0049716 A1 | | 3/2003 | Barton et al. |

OTHER PUBLICATIONS

Herndon et al., Treatment of Burns, Curr. Probl. Surg., 1987, vol. 2, pp. 347–397.
Wolfe R.R., Nutrition and Metabolism in Burns, In Chernow B. and shoemaker W.C., eds., Critical Care, State of the Art, Fullerton, California, Society of Critical Care Medicine, 1986, vol. 7, pp. 19–61, (Chernow & Shoemaker, eds.).
Fox et al. (1962), J. Clin. Endocrinol. Metab. 22: 921–924.
Karim et al. (1973), Clin. Pharmacol. Ther. 14:862–869.
Roubeoff et al. (1991), Nutrition Reviews 49 (6) : 163–175.
Kopera H. (1985), Acta Endocrinologica, Supplementum 271:11–18.
Garlick et al. In Ballier's Clinical Gastroenterology, Burns ed., vol. 2, No. 4, 1988, pp. 915–940 (Burns, ed.).
Haupt et al. (1984), The American Journal of Sports Medicine 12 (6) :469–484.

Wilson, J.D. in Goodman and Gilman's, The pharmacological Basis of Therapeutics, Eight Edition, Pergamon Press, 1990, pp. 1413–1430.
Demling et al., Current Opinion in Critical Care (1996) 2:482–491.
Kowalewski et al., Acta Endocrinologica (1970) 64: 541–547 (1974).
Marmo et al., Gazzetta Medica Italiana (in Italian) (1974) 133:47–57—13a English translation.
Albanese et al., Nutrition Reports International (1970) 1 (4) :213–242.
O'Shea et al., Nutrition Report International (1970) 2 (6) : 351–362.
Selye, Exp. Med. Surg., 28(2), 169–78 Abstract Only, (1988).
Solymoss et al. Toxicol. Appl. Pharmacol., 18(3),586–92 Abstract Only, (1987).
FDA Approved Physician's Product Brochure No. 43 for ANAVAR® Brand of Oxandrolone, including Package Insert, G.D. Searle (1964) (Exhibit 3).
Berkowitz, D., Clinical Investigator's Report, Apr. 25, 1962 (Exhibit 4).
Ruffin, J.M., Clinical Investigator's Report, Mar. 20, 1962 (Exhibit 5).
Mensch, M., Clinical Investigator's Report, Aug. 23, 1962 (Exhibit 6).
Woolery, J.W., Clinical Investigator's Report, Apr. 27, 1962 (Exhibit 7).
Fox, M., Minot, A.S., and Liddle, G.W., (1962) Oxandrolone: A Potent Anabolic Steroid of Novel Chemical Configuration, J. Clin. Endocrinol, Metab., vol. 22, pp. 921–924 (Exhibit 8).
Metcalf, W., Clinical Investigator's Report, Jul. 14, 1961 (Exhibit 9).
Albanese, A.A., Lorenze, E.J., and Orto, L.A., (May 15, 1962) Nutritional and Metabolic Effects of Some Newer Steroids, Oxandrolone and Triamcinolone, New York State J. Med. 62:1607–1613 (Exhibit 10).
Kasler, M.H., Clinical Investigator's Report, Mar. 16, 1962 (Exhibit 11).
Paulsen, C.A., Clinical Investigator's Report, Mar. 9, 1962 (Exhibit 12).

(List continued on next page.)

Primary Examiner—Frederick Krass
Assistant Examiner—Amy Lewis
(74) Attorney, Agent, or Firm—John P. White; Cooper & Dunham LLP (57) ABSTRACT

The subject invention provides a method of treating burn-induced weight loss in a burn patient which comprises administering a therapeutically effective amount of an oxandrolone to the patient. The invention also provides a method of treating a wound in a patient suffering from a wound which comprises administering a therapeutically effective amount of an oxandrolone to the patient. The subject invention further provides a method of treating burn-induced weight loss in a burn patient which comprises administering a therapeutically effective amount of an oxandrolone in conjunction with a protein supplement to the patient.

33 Claims, 9 Drawing Sheets

OTHER PUBLICATIONS

Gold, E.M., Clinical Investigator's Report, May 31, 1962 (Exhibit 13).

Heller, C.G., Clinical Investigator's Report, Jun. 20, 1962 (Exhibit 14).

Leevy, C.M., Clinical Investigator's Report, Aug. 24, 1961 (Exhibit 15).

DeBiasse and Wilmore, (May 1994), "What is Opitmal Nutritional Support?," New Horizons, vol. 2, No. 2, pp. 122–130 (Exhibit 1).

Furst et al., (Nov. 1989), "Evidence for a Nutritional Need for Glutamine in Catabolic Patients," Kidney Int Suppl., vol. 27, pp. 287–292 (Exhibit 2).

Keys et al., (1950), The Biology of Human Starvation, University of Minnesota Press, Minneapolis, vol. 1, pp. VII–IX, vol. 2, pp. VII–VIII, 1345–1385 (Table of Contents and Index Only) (Exhibit 3).

Moore, (1959), Metabolic Care of the Sugical Patient, W.B. Saunders Company, Philadelphia and London, pp. IV–V, 991–1011 (Table of Contents and Index Only) (Exhibit 4).

Roberts and Zolaga, (May 1994), "Dietary Bioactive Peptides," New Horizons, vol. 2, No. 2, pp. 237–243 (Exhibit 5).

Ziegler, (May 1994), "Growth Hormone Administration During Nutritional Support: What is to be Gained?," New Horizons, vol. 2, No. 2, pp. 244–256 (Exhibit 6).

May 14, 1999 letter from the Department of Health and Human Services, Center for Drug Evaluation and Research, Rockville, Maryland, providing a "Copy of All Disclosable Approval Information For the Product Oxandrin, Manufactured by Biotechnology General," 30 pages (Exhibit 7).

G.D. Searle & Co., (1962), Physicians' Product Brochure No. 43, "ANAVAR® Brand of Oxandrolone, For Protein Tissue Building and Anabolism," 16 pages with a 5 page insert (Exhibit 8).

Arora and Rochester, (1982), "Respiratory Muscle Strength and Maximal Voluntary Ventilation in Undernourished Patients," Am Rev Respir Dis., vol. 126, p. 5–8 (Exhibit 1).

Aulick and Wilmore, (May 1979), "Increased Peripheral Amino Acid Release Following Burn Injury," Surgery, vol. 85, pp. 560–565 (Exhibit 2).

Bessey et al., (1989), "Post Traumatic Skeletal Muscle Proteolysis: The Role of the Hormonal Environment," World J. Surg., vol. 13, pp. 465–470 (Exhibit 3).

Bistrian, (Nov. 11, 1974), "Protein Status of General Surgical Patients," JAMA, vol. 230, pp. 858–860 (Exhibit 4).

Chandra, (Mar. 26, 1973), "Nutrition, Immunity, and Infection: Present Knowledge and Future Directions," Lancet, pp. 688–691 (Exhibit 5).

Daly, (1991), "Malnutrition," in American College of Surgeons Scientific American Surgery, Scientific American, Inc., New York, pp. 12–1—12–18 (Exhibit 6).

Demling and DeBiasse, (Jul. 1995), "Micronutrients in Critical Illness," Crit Care Clin North Am., vol. 11, No. 3, pp. 651–673 (Exhibit 7).

Evans et al., (1983), "Protein Metabolism and Endurance Exercise," Phys Sport Med, vol. 11, pp. 63–67, 71–72 (Exhibit 8).

Fox et al., (1962), "Oxandrolone: A Potent Anabolic Steroid of Novel Chemical Configuration, " J. Clin. Endocrinol Metab., vol. 22, pp. 921–924 (Exhibit 9).

Frontera et al., (1988), "Strength Conditioning in Older Men: Skeletal Muscle Hypertrophy and Improved Function," J. Appl. Physiol, vol. 64, No. 3, pp. 1038–1044 (Exhibit 10).

Gatzen, et al., (1992), "Growth Hormone Attenuates the Abnormal Distribution of Body Water in Critically Ill Surgical Patients," Surgery, vol. 112, pp. 181–187 (Exhibit 11).

Gontzea, (Jul. 1974), "The Influence of Muscular Activity on Nitrogen Balance and on the Need of Man of Proteins," Nutr Rep. Int., vol. 10, pp. 35–43 (Exhibit 12).

Herndon et al., (Oct. 1988), "Effect of Propranolol Administration on Hemodynamic an Metabolic Response of Burned Pediatric Patients," Ann Surg., vol. 208, pp. 484–492 (Exhibit 13).

Herndon et al., (Oct. 1990), "Effect of Recombinant Human Growth Hormone on Donor Site Healing in Severely Burned Children," Ann Surg., vol. 212, pp. 424–431 (Exhibit 14).

Hickson et al., (1995), "Glutamine Prevents Down–Regulation of Myosin Heavy Chain Synthesis and Muscle Atrophy From Glucocorticoids," Am J Physiol, vol. 268, pp. 730–734 (Exhibit 15).

Jahoor et al., (1988), "Dynamics of the Protein Metabolic Response to Burn Injury," Metabolism, vol. 37, No. 4, pp. 330–337 (Exhibit 16).

Jeevanadam et al., (May 1992), "Decreased Growth Hormone Levels in the Catabolic Phase of Severe Injury," Surgery, vol. 111, pp. 495–502 (Exhibit 17).

Karim et al., (1973), "Oxandrolone Disposition and Metabolism in Man, "Clin. Pharmacol Ther., vol. 14, pp. 862–869 (Exhibit 18).

Knox et al., (1995), "Increased Survival After Major Thermal Injury: the Effect of Growth Hormone Therapy in Adults," J. Trauma, vol. 39, No. 3, pp. 526–532 (Exhibit 19).

Kopera, (1985), "The History of Anabolic Steroids and a Clinical Review of Clinical Experiences," Acta Endocrinol., vol. 271, pp. 11–18 (Exhibit 20).

Lacey and Wilmore, (Aug. 1990), "Is Glutamine a Conditionally Essential Amino Acid?," Nut rev, vol. 48, No. 8, pp. 297–309 (Exhibit 21).

Lemon, (1987), "Protein and Exercise Update 1987," Medicine and Science in Sports and Exercise, vol. 19, pp. 179–190 (Exhibit 22).

Mendenhall et al., (1993), "A Study of Oral Nutritional Support With Oxandrolone in Malnourished Patients with Alcoholic Hepatitis: Results of a Department of Veteran Affairs Cooperative Study," Hepatology, vol. 17, No. 4, pp. 564–576 (Exhibit 23).

Mendenhall et al., (Dec. 6, 1984), "Short–Term and Long–Term Survival in Patients With Alcoholic Hepatitis Treated with Oxandrolone and Prenisolone," N. Engl. J. Med., vol. 311, pp. 1464–1470 (Exhibit 24).

Meridith et al., (1989), "Dietary Protein Requirements and Protein Metabolism in Endurance–trained Men," J Appl Physiol, vol. 66, No. 6, pp. 2850–2856 (Exhibit 25).

Newsome et al., (Aug. 1973), "Weight Loss Following Thermal Injury," Ann Surg., vol. 178, pp. 215–217 (Exhibit 26).

Reichsman and Evans, (1991), "Muscle Protein Changes Following Eccentric Exercise in Humans," Eur J Appl Physiol., vol. 62, No. 4, pp. 245–250 (Exhibit 27).

Shernan et al., (1989), "Growth Hormone Enhances Reepithelialization of Human Split–Thickness Skin Graft Donor Sites," Surg Forum, vol. 40, pp. 37–39 (Exhibit 28).

Souba et al., (Jan. 1990), "Oral Glutamine Reduces Bacterial Translocation Following Abdominal Radiation," J Surg Res., vol. 48, No. 1, pp. 1–5 (Exhibit 29).

Stehle et al., (Feb. 4, 1989), "Effect of Parenteral Glutamine Peptide Supplements on Muscle Glutamine Loss in Nigrogen Balance After Major Surgery," *Lancet*, vol. 1, pp. 231–233 (Exhibit 30).

Studley, (Feb. 8, 1936), "Percentage of Weight Loss: A Basic Indication of Surgical Risk in Patients with Chronic Peptic Ulcers," *JAMA*, vol. 106, pp. 458–460 (Exhibit 31).

Watters et al., (Feb. 1986), "Both Inflammatory and Endocrine Mediators Stimulate Host Response to Sepsis," *Arch Surg.*, vol. 121, pp. 179–190 (Exhibit 32).

Welbourne, (May 1995), "Increased Plasma Bicarbonate and Growth Hormone After an Oral Glutamine Load," *Am J Clin Nutr*, pp. 1058–1061 (Exhibit 33).

Wernerman et al., (1989), "Glutamine and Ornithine–Alpha–Ketoglutarate but not Branched–Chain Amino Acids Reduce the Loss of Muscle Glutamine After Surgical Trauma," *Metabolism*, vol. 38, pp. 63–66 (Exhibit 34).

Wilmore et al., (Jun. 1974), "Anabolic Effects of Human Growth Hormone and High Caloric Feedings Following Thermal Injury," *Surg. Gynecol Obstet.*, vol. 138, pp. 875–884 (Exhibit 35).

Wilmore et al., (Oct. 1974), "Catecholamines: Mediator of the Hypermetabolic Response to Thermal Injury," *Ann Surg.*, vol. 180, pp. 653–669 (Exhibit 36).

Wilmore et al., (1977), "Influence of the Burn Wound on Local and Systemic Responses to Injury," *Ann Surg.*, vol. 186, No. 4, pp. 444–458 (Exhibit 37).

Wilmore and Aulick, (Dec. 1978), "Metabolic Changes in Burned Patients," *Surg Clin North Am.*, vol. 58, No. 6, pp. 1173–1187 (Exhibit 38).

Wilmore, (1980), "Feeding the Patient," in *The Metabolic Management of the Critically Ill*, Plenum Medical Books Co., New York, Wilmore Ed., pp. 171–233 (Exhibit 39).

Ziegler et al., (1992), "Clinical and Metabolic Efficacy of Glutamine–Supplemented Parenteral Nutrition After Bone Marrow Transplantation," *Ann Intern Med.*, vol. 116, pp. 821–828 (Exhibit 40).

U.S. Appl. No. 10/799,264, filed Mar. 12, 2004, Fishbein (Exhibit 6).

U.S. Appl. No. 10/799,197, filed Mar. 12, 2004, Fishbein (Exhibit 7).

*Chicago Tribune*, (Sep. 20, 1991), North Sports Final edition, Business Section, p. 1 (Exhibit 8).

Demling and DeSanti, (1997), "Oxandrolone, an Anabolic Steroid, Significantly Increases the Rate of Weight Gain In the Recovery Phase After Major Burns," *J. Trauma*, vol. 43, No. 1, pp. 47–51 (Exhibit 9).

Demling and De Santi, (Oct. 1998), "Closure of the 'Non–Healing Wound' Corresponds with Correction of Weight Loss Using the Anabolic Agent Oxandrolone, " *Ostomy/Wound Management*, vol. 44, No. 10, pp. 58–60, 62, 64, 66, 68 (Exhibit 10).

Demling, (1999), "Comparison of the Anabolic Effects and Complications of Human Growth Hormone and the Testosterone Analog, Oxandrolone, After Severe Burn Injury," vol. 25, pp. 215–221 (Exhibit 11).

Demling, (Mar.–Apr. 2000), "Oxandrolone, an Anabolic Steroid, Enhances the Healing of a Cutaneous Wound in the Rat," *Wound Repair Regen.*, vol. 8, No. 2, pp. 97–102 (Exhibit 12).

Demling and DeSanti, (2001), "The Rate of Restoration of Body Weight After Burn Injury, Using the Anabolic Agent Oxandrolone, is not Age Dependent," *Burns*, vol. 17, pp. 46–51 (Exhibit 13).

Demling and DeSanti, (Sep./Oct. 2001), "The Anabolic Steroid, Oxandrolone, Reverses the Wound Healing Impairment in Corticosteroid–Dependent Burn and Wound Patients," *Wounds*, vol. 13, No. 5, pp. 203–207 (Exhibit 14).

DeSanti et al., (1998), "Development of a Burn Rehabilitation Unit: Impact on Burn Center Length of Stay and Functional Outcome," Journal of Burn Care & Rehabilitation, vol. 19, No. 5, pp. 414–419 (Exhibit 15).

Ehrlich and Hunt, (Aug. 1969), "The Effects of Cortisone and Anabolic Steroids on the Tensile Strength of Healing Wounds," *Ann Surg.*, vol. 170, No. 2, pp. 203–206 (Exhibit 16).

Eisenberg, (1966), 65 *Chemical Abstracts*:40387 (Exhibit 17).

Eisenberg, (May 1966), "Effects of Androgens, Estrogens and Corticoids on Strontium Kinetics in Man," *J. Clin. Endocr.*, vol. 26, pp. 566–572 (Exhibit 18).

Ferraresi, (Apr. 1996), "Clinical Profile of Oxandrin," BTG Pharmaceuticals (Exhibit 19).

Grant, (1980), "Patient Selection," *Handbook of Total Parenteral Nutrition*, Saunders, pp. 7–46 (Exhibit 20).

Hausmann et al., (Mar./Apr. 1990), "Anabolic Steroids in Polytrauma Patients. Influence on Renal Nitrogen and Amino Acid Losses: A Double Blind Study, " *J. Parent. Enteral. Nutr.*, vol. 14, No. 2, pp. 111–114 (Exhibit 21).

Helfman and Falanga, (Aug. 1995), "Stanozolol as a Novel Therapeutic Agent in Dermatology," *J. of the American Acad. of Dermatology*, vol. 33, No. 2, pp. 254–258 (Exhibit 22).

Jekot and Purdy, (Apr. 1993), "Treating HIV/AIDS Patients with Anabolic Steroids," *AIDS Patient Care*, pp. 68–74 (Exhibit 23).

Koehler et al., (1998), "Achieving Healing of Non–Healing Pressure Ulcers," 1998 WOCN 30th Annual Conference, p. 37 (Exhibit 24).

Kotler, (1996), "Dilemmas in the Treatment of Weight Loss," BTG Pharmaceuticals, pp. 1–7 (Exhibit 25).

Levien et al., (Jul. 1994), "Reviews of Trimetrexate and Oxandrolone," *Hospital Pharmacy*, vol. 29, No. 7, pp. 696–702, 705–708 (Exhibit 26).

Martindale, (1982), *The Extra Pharmacopoeia 28$^{th}$ Edition*, The Pharmaceutical Press, London, Reynolds and Prasad Eds., p. 1430 (Exhibit 27).

PR Newswire, 0828P8715, (Aug. 28, 1991), "Gynex Obtains International Rights to Drug to Treat For Growth Disorders, AIDS" (Exhibit 28).

Schwartz and Miller, (1986), "Androgens and Anabolic Steroids," in *Modern Pharmacology, Second Edition*, Little Brown and Company, Boston/Toronto, Craig and Stitzel Eds., pp. 905–924 (Exhibit 29).

Tennenbaum and Shklar, (Dec. 1970), "The Effect of an Anabolic Steroid on the Healing of Experimental Extraction Wounds," *Oral Surg.*, vol. 30, No. 6, pp. 824–834 (Exhibit 30).

Udupa and Chansouria, (Mar. 1969), "Studies on Wound Healing," *Indian J. Med. Res.*, vol. 57, pp. 434–456 (Exhibit 31).

PDR 38 Edition 1984 Physicians' Desk References pp. 1840–1841 (Exhibit 1).

PDR 42 Edition 1988 Physicians' Desk References pp. 1975–1976 (Exhibit 2).

* cited by examiner

FIGURE 1

RESPONSE TO BURN INJURY, MET-Rx, OXANDRIN

| | | | CATABOLIC PHASE | | | ANABOLIC PHASE | | | | | | | | |
|---|---|---|---|---|---|---|---|---|---|---|---|---|---|---|
| | AGE | BURN %BSA | CATABOLIC PHASE (DAYS) | WEIGHT LOSS (LBS) | %TOTAL | ONSET | ENERGY LEVEL | | | | THERAPY INDEX | | | |
| | | | | | | | | 1 | 2 | 3 (wks) | | 1 | 2 | 3 (wks) |
| GROUP 1 n=10 | 25±9 | 35±9 | 38±9 | 30±5 | 18±3 | 1 | | 2±1 | 2±1 | 3±2 | | 2±1 | 3±1 | 3±1* |
| GROUP 2 MET-Rx n=7 | 28±8 | 38±9 | 37±11 | 28±6 | 17±4 | 2 | | 4±1* | 6±2* | 7±2* | | 3±1 | 6±1* | 6±2* |
| GROUP 3 MET-Rx, Oxandrin n=4 | 27±10 | 37±10 | 36±10 | 29±5 | 18±4 | 3 | | 5±1* | 8±2* | 8±2* | | 4±1* | 7±1* | 8±2* |

*significant difference between groups p<0.05

RESPONSE TO BURN INJURY, MET-Rx, OXANDRIN

| | CATABOLIC PHASE NUTRITIONAL PROFILE | | | | | | ANABOLIC PHASE | | | | | |
|---|---|---|---|---|---|---|---|---|---|---|---|---|
| | Cal+ kg/day | Prot g/kg/day | Cal/kg/day+ | | | Prot g/kg/day | | | Weight Gain (lbs) | | | |
| | | | 1 | 2 | 3 (wks) | 1 | 2 | 3 (wks) | 1 | 2 | 3 (wks) |
| GROUP 1 (n=10) | 30±2 | 1.9±0.02 | 22±2 | 23±2 | 23±3 | 1.3±0.1 | 1.3±0.1 | 1.2±0.1 | 1.2±0.1 | 1.3±0.2 | 1.4±0.2 |
| GROUP 2 (n=7) | 31±3 | 2.0±0.2 | 24±3 | 27±2* | 28±3* | 2.0±0.2 | 2.1±0.1 | 2.2±0.2 | 2.5±0.2* | 2.7±0.1* | 2.9±0.2* |
| GROUP 3 (n=4) | 31±3 | 1.9±0.1 | 25±2 | 28±2* | 30±3* | 2.1±0.1 | 2.1±0.1 | 2.2±0.1 | 4.9±0.5* | 5.0±0.5* | 5.1±0.5* |

*significant difference between groups p<0.05
+non-protein calories

EFFECT OF ANABOLIC AGENT AND INCREASED PROTEIN CONTENT ON THE RECOVERY PHASE

| | CATABOLIC PHASE | | | | | RECOVERY (ANABOLIC) PHASE (WKS) | | | | | | | | | |
|---|---|---|---|---|---|---|---|---|---|---|---|---|---|---|---|
| | | | | | | NUTRITIONAL PROFILE | | | | | | | WEIGHT GAIN | | |
| | | | | | | Cal/kg/day+ | | | Prot/g/kg/day | | | Pounds Per Week | | | |
| | AGE | BURN %BSA | DAYS | WT. LOSS LBS. | %TOTAL | 1 | 2 | 3 | 1 | 2 | 3 | 1 | 2 | 3 |
| Group 1 (n=6) | 34±8 | 45±8 | 39±9 | 20±7 | 12±4 | 32±4 | 34±4 | 35±5 | 1.9±0.1 | 2±0.2 | 2.2±0.1 | 2.5±0.2 | 2.6±0.4 | 2.6±0.5 |
| Group 2 (n=7) | 36±9 | 47±6 | 35±9 | 21±6 | 11±3 | 33±3 | 33±4 | 34±4 | 2.0±0.2 | 2.0±0.2 | 2.2±0.2 | 3.9±0.4* | 4.4±0.5* | 4.8±0.5* |
| Group 3 (n=10) | 39±8 | 42±7 | 32±10 | 19±8 | 11±6 | 34±3 | 33±3 | 33±5 | 1.5±0.2+ | 1.4±0.2+ | 1.4±0.3+ | 1.2±0.1+ | 1.3±0.2+ | 1.4±0.2+ |

* significant difference between groups 1 and 2 $p<0.05$
+ significant difference between groups 1 and 3 $p<0.05$

USE OF OXANDROLONE IN THE TREATMENT OF BURNS AND OTHER WOUNDS

This application is a continuation of U.S. Ser. No. 08/985,734, filed Dec. 5, 1997, now U.S. Pat No. 6,576,659 which claims priority of U.S. Provisional Application Ser. No. 60/032,414, filed on Dec. 5, 1996, the contents of which are hereby incorporated into this application by reference.

Throughout this specification, various publications are referenced by Arabic numerals within parentheses. Full citations for these references may be found at the end of the specification immediately preceding the claims. The disclosure of these publications in their entireties are hereby incorporated by reference into this specification in order to more fully describe the state of the art to which this invention pertains.

BACKGROUND OF THE INVENTION

Burns

Over one million people are involved in burn accidents in the United States each year. Approximately 150,000 of these patients are hospitalized and over 6000 of these die each year (1).

Following thermal injury, severe protein and fat wasting occurs (1). Loss of as much as 20% of body protein may occur in the first two weeks following major burn injury (2). Increased oxygen consumption, metabolic rate, urinary nitrogen excretion, fat breakdown and steady erosion of body mass are all directly related to burn size and return to normal as the burn wound heals or is covered (1). The metabolic rate in patients with burns covering more than 40% of total body surface is twice as high as the metabolic rate in people without burns (1).

Although the danger associated with acute burn-induced weight loss, especially lean body mass has well been defined, the impact of this process on patient outcome continues to be severely underestimated. The focus of management of critical illness post-burn remains that of cardiopulmonary support and infection control while stress induced catabolism may proceed unchecked leading to a rapid loss of lean tissue (fat-free), mainly muscle which is followed by protein loss in diaphragm, heart, then liver, kidney and splanchnic bed. The loss of visceral proteins may actually begin very early after injury and the muscle protein is used to replace organ losses. It is clear that the response to severe injury or post-surgical infection will become auto-destructive if not contained. Complications will occur including multiple organ dysfunction, the leading cause of death in the post-burn period. A loss of lean body mass exceeding 40% of total is usually fatal. This muscle loss corresponds to a comparable loss of total body protein which affects all organ functions.

Although major advances in surgical nutrition have also been made, attempt at controlling the protein loss often come too little and too late to prevent the catabolism induced complications. The degree of lean tissue loss corresponds very precisely with not only profound weakness, including chest wall and diaphragm impairment, but also decreased immune function, leading to infection, usually pneumonia. Both lymphocyte and neutrophil immune defenses are impaired. Loss of myocardial muscle leads to decreased contractility. Wound healing becomes markedly impaired and an open wound soon becomes an infected wound. Cell metabolic abnormalities occur including decreased cell energy charge and impaired calcium kinetics.

Despite this well defined concept, a routine assessment of body weight and body protein loss and an aggressive attempt at preventing early protein depletion by controlling the host response to injury and optimizing anabolism is not performed.

The current therapy of burn injury, namely high protein nutrition and early wound closure attenuates the process but patients with large burns enter the recovery phase with a significant deficit in muscle mass. Since the peak rate of restoration of muscle mass, using endogenous stimuli alone, including good nutrition approximates 1 to 1.5 pounds a week, restoration of lean body mass usually requires months.

Use of the anabolic agent, human growth hormone, can increase anabolic activity in the burns, but high expense and complications such as hyperglycemia have prevented widespread use of this agent (3). This agent also has to be administered by injection.

Since the rate of recovery of lean body mass dictates disability time, an increased rate would be of tremendous functional and economic value in burn patients.

The subject invention provides therapies that increase the rate of recovery of lean body mass, thereby reducing the length of stay in a hospital and reducing rehabilitation time. Moreover, the subject invention provides therapies that increase the rate of wound healing. This is of great importance in burn-patients, especially in those patients that receive skin grafts. This is also important in burn-patients which have wounds at donor sites.

Oxandrolone

Oxandrolone (17-methyl-17-hydroxy-2-oxa-5-androstan-3-one) is a known compound which is commercially available. The preparation of oxandrolone is described, inter alia, in U.S. Pat. No. 3,128,283. Oxandrolone is an anabolic steroid synthetically derived from testosterone. Oxandrolone has a unique chemical structure compared with other testosterone analogs. Oxandrolone contains an oxygen rather than a carbon atom at the 2-position within the phenanthrene nucleus (4) and lacks a 4-ene function in the A-ring. The anabolic activity of oxandrolone is approximately 6 times greater than its androgenic activity and has been found to be 6.3 times greater than that of methyltestosterone (4).

Anabolic activity refers to the ability to cause nitrogen retention, promoting weight gain and increasing muscle strength. Androgenic activity refers to the ability to enhance male characteristics (i.e. secondary sex characteristics such as facial hairs and voice changes). Because of the high ratio of anabolic to androgenic activity, oxandrolone is less likely to cause adverse cosmetic consequences in women than many testosterone analogs.

Furthermore, in contrast to the majority of oral androgenic anabolic steroids (e.g. micronized testosterone, methyltestosterone, fluoxymesterone), oxandrolone undergoes relatively little hepatic metabolism (5, 6).

Oxandrolone has been administered to malnourished patients with alcoholic hepatitis (7, 8). Oxandrolone has been shown to be safe even in dosages of up to 80 mg/day in patients with alcoholic hepatitis (7).

The subject invention discloses the use of an oxandrolone for the treatment of cachexia, muscle wasting and involuntary weight loss associated with wounds, especially burns.

SUMMARY OF THE INVENTION

The invention also provides a method of treating a wound in a patient suffering from a wound which comprises administering a therapeutically effective amount of an oxandrolone to the patient.

The subject invention provides a method of treating burn-induced weight loss in a burn patient which comprises administering a therapeutically effective amount of an oxandrolone to the patient.

The subject invention further provides a method of treating burn-induced weight loss in a burn patient which comprises administering a therapeutically effective amount of an oxandrolone in conjunction with a protein supplement to the patient.

DETAILED DESCRIPTION OF THE INVENTION

Oxandrolone as used herein encompasses 17-methyl-17-hydroxy-2-oxa-5-androstan-3-one (both racemic mixtures and optically active enantiomers) as well as pharmaceutically acceptable esters thereof. For example, an oxandrolone product which is commercially available is the Oxandrin tablet from BTG Pharmaceuticals Corp., Iselin, N.J. 08830, which is 17α-methyl-17β-hydroxy-2-oxa-5α-androstan-3-one. This product was used throughout the studies described herein.

Protein supplement as used herein encompasses any nutritionally effective protein supplement including commercially available protein supplements.

Protein supplement Met-Rx™ contains 74 gram/liter protein, 48 gram/liter carbohydrate and 8 gram/liter fat.

A wound as used herein is a breach in the continuity of skin tissue. Examples of wounds are punctures, incisions, excisions, lacerations, abrasions, ulcers and burns. Examples of ulcers as used herein are ulceration of the heel in a diabetic patient and decubitus ulcers in bedridden patients.

A skin graft as used herein encompasses an autograft or an allograft.

Oxandrolone may be administered orally, intravenously, intramuscularly, subcutaneously, topically, intratracheally, intrathecally, intraperitoneally, rectally, vaginally or intrapleurally.

If oxandrolone is administered orally, it is administered in the form of a tablet, a pill, a liquid or a capsule.

A liquid may be administered in the form of a solution or a suspension.

The compositions produced in accordance with the invention may comprise conventional pharmaceutically acceptable diluents or carriers. Tablets, pills, liquids and capsules may include conventional excipients such as lactose, starch, cellulose derivatives, hydroxypropyl methylcellulose and magnesium stearate. Suppositories may include excipients such as waxes and glycerol. Injectable solutions will comprise sterile pyrogen-free media such as saline and may include buffering agents, stabilizing agents, solubilizing agents or preservatives. Conventional enteric coatings may also be used.

Compositions for topical administration may be in the form of creams, ointments, lotions, solutions, transdermal delivery systems, transdermal patches or gels.

The subject invention provides a method of treating burn-induced weight loss in a burn patient which comprises administering a therapeutically effective amount of an oxandrolone to the patient.

The subject invention further provides a method of treating burn-induced weight loss in a burn patient which comprises administering a therapeutically effective amount of an oxandrolone in conjunction with a protein supplement to the patient.

The subject invention provides a use of an oxandrolone in the preparation of a composition to treat burn-induced weight loss in a burn patient. This composition may optionally comprise a protein supplement.

In a preferred embodiment, the amount of oxandrolone is about 1–100 mg per day.

In especially preferred embodiments, the amount of oxandrolone is about 20 mg per day or about 80 mg per day.

The oxandrolone may be administered in a solid dosage form, in a liquid dosage form, in a sustained-release formulation or in a once a day formulation. The liquid dosage form may inter alia be alcohol-based or formulated with a cyclodextrin such as hydroxypropyl-β-cyclodextrin.

The invention further provides a method of treating a wound in a patient suffering from a wound which comprises administering a therapeutically effective amount of an oxandrolone to the patient.

The subject invention provides a method of improving the rate of healing of a wound in a patient suffering from a wound which comprises administering a therapeutically effective amount of an oxandrolone to the patient.

The subject invention further provides a use of an oxandrolone in the preparation of a composition to treat a wound in a patient suffering from a wound.

The subject invention also provides a use of an oxandrolone in the preparation of a composition to improve the rate of healing of a wound.

The subject invention also describes the use of oxandrolone in the maintenance and restoration of lean body mass in burn and trauma patients.

The wound may be a burn wound, an ulcer especially a decubitus ulcer (pressure sore), a skin graft or any form of wound including a traumatic wound.

Oxandrolone may be administered in conjunction with glutamine or human growth hormone.

The subject invention further provides a composition for use in topical treatment of wounds comprising an oxandrolone and a pharmaceutically acceptable carrier.

Such topical composition may be used for the treatment of wounds including burns and ulcers especially decubitus ulcers (pressure sores).

EXAMPLES

The Examples which follow are set forth to aid in understanding the invention but are not intended to, and should not be construed to, limit its scope in any way.

Example 1
The Effect of Oxandrolone on Post-burn Catabolism (I)

A study on the effect of oxandrolone on post-burn patients was performed as described below.

Patient Characteristics

Patients included in the study had a deep burn of 30–50% of body surface.

The patients included in this study had undergone:

a. catabolic phase until 80–90% of wound closure (4–10 weeks);
b. loss of 15–25% body weight (mostly lean body mass) during catabolic phase despite optimum nutrition;

The recovery of anabolic phase usually last 8–16 weeks with peak anabolism in the first 8 weeks.

The transition from "catabolic" to recovery "anabolic" was defined by:

a. No need for life support measures, being stable and out of the Intensive Care Unit (ICU);
b. No active infection (stress);
c. Open wound (not counting donor sites) not exceeding 10% Total Body Surface (TBS);
d. Patient taking oral diet with supplements or tube feeding (off parenteral feeding);
e. patient can actively participate in a physical therapy program with active ROM exercises accentuating the anabolic stimulus of exercise.

All patients were located in the burn step-down unit or in an acute rehabilitation hospital where daily information is retrieved from the physiatrist, nutritionist, and therapist.

The patients were divided into three groups in a prospective randomized manner:

Group 1: Standard nutritional goals as defined by the nutrition support service.
Group 2: Same as Group 1 plus 2–3 Met-Rx™ (protein supplement) per day (sufficient protein to increase daily protein intake to 2–2.2 g/kg/day)
Group 3: Same as Group 2 plus oxandrolone 20 mg orally four times daily.

Measurements

The following factors were checked:

a. Subjective energy level (per Braintree study) 0–10;
b. Physical therapy index[1] (per Braintree study) 0–10:
  0 completes 25% session with fatigue
  2 completes 50% session with fatigue
  4 completes 75% session with fatigue
  6 completes 100% session with fatigue
  8 completes 100% session with no fatigue
  10 completes 100% session and more with no fatigue;
c. Weekly weight gain;
d. Daily nutritional profiles;
e. Measurement of lean body mass by bioelective impedance.

The onset of the study was defined as the onset of the recovery phase (anabolic phase). Patients were studied for 3 weeks (from the onset of anabolism).

Results

The results are shown in FIGS. 1–6 and are described below:

1. The response to the catabolic phase was an 18% body weight loss despite optimum nutrition. The predicted amount of muscle loss is 70% of total loss since 4 lbs muscle are lost for 1 lb of fat.
2. The subjective energy level at the end of catabolism was 1–2 as expected.
3. Calorie and protein intake:
  Group I
    (10 patients):
      Despite high calorie, high protein diets and supplements or tube feedings, the calorie intake was below 25 cal/kg and protein intake below .5 g/kg protein. Patients were generally anorexic, felt full and did not like the supplements. Energy level and therapy index remained low for three weeks.
  Group II
    (7 patients):
      All patients liked the Met-Rx™ and actually ate better overall. Non-protein caloric intake improved slightly but significantly while protein intake doubled. Subjective energy level and quality of therapy were markedly increased and weight gain was double that of Group I unaccountable by the modest increase in calories alone.
  Group III
    (4 patients):
      Nutritional profile was comparable to Group II with an apparent added stimulus to food intake. Weight gain was four times that of Group I and energy level and therapy markedly improved.

Thus, increased protein intake in the form of Met-Rx™ markedly improved the rate of functional return in the recovery period. Attempt at improving nutrition with other standard nutrients was unsuccessful. The combination of Met-Rx™ and oxandrolone results in a great weight gain considered to be 80% lean body weight gain by bioelective impedance measurements.

Example 2
The Effect of Oxandrolone on Post-Burn Catabolism (II)

Another study on the effect of oxandrolone on post-burn patients was carried out as follows.

Patient Characteristics patients included in the study had a deep burn of 30–50% of body surface, reached recovery phase in about 4–6 weeks post-burn and required hospitilization for at least 3 weeks during the recovery phase.

The onset of the study was defined as the onset of the recovery phase (anabolic phase). The study period included the first three weeks of the recovery phase. Although somewhat arbitrary, the beginning of the recovery period was determined for all the patients using the following criteria:

a. No need for life support measures, with a stable cardiopulmonary status;
b. No active infection;
c. Basal body temperature below 99.5° F.;
d. Metabolic rate at rest (indirect calorimetry) being less than 130% of normal;
e. Open wound (not counting donor sites) not exceeding 10% TBS;
f. Patient taking adequate oral diet with supplements or tube feeding and off all parenteral feeding;

g. active participation in a physical therapy program including resistance exercises especially to large muscle groups.

The patients were divided into three groups in a prospective randomized manner:

Group 1:
High protein high calorie ad lib oral diet and protein supplement Met-Rx™. The supplement was given in a quantity equal to approximately one liter so that total protein intake would approximate 2 g/kg/day.

Group 2:
Same as Group I with the addition of oxandrolone 10 mg orally twice a day.

Group 3:
ad lib oral diet and a protein hydrolysate supplement (Ensure-HN or Sustacal). These supplements contain approximately 40–45 g/l protein, 140–150 g/l carbohydrate and 30–37 g/l fat. Daily protein intake consumed equalled 1.3–1.5 g/kg or 75% above the RDA value for healthy normals of 0.8 g/kg. This group was managed in the ten months prior to the onset of this study.

All patients were located in the burn/trauma step-down unit and then transferred to an acute rehabilitation hospital usually within the first week of onset of the recovery period. A burn nurse coordinator followed all patients at the rehabilitation hospitals. All patients were monitored until discharge but only the first three week period was used for the study period.

Measurements

The following factors were checked:

a. Fatigue was measured objectively through increases in pulse of over 75% of predicted maximum (based on age) and a respiratory rate exceeding 30 breaths per minute beyond one minute after completion of the activity.

b. Muscle function was quantitated using a physical therapy index. The physical therapy program was determined for each patient by the burn therapist team based on optimum projected goals to be achieved at the three week period. Standard isokinetic and resistance exercises were used to increase strength. Ambulation, stair climbing and the stationary bike were used to increase endurance. Since the basic components of therapy programs were nearly identical between patients, an index was developed which quantitated progress of patient performance:

0 completes 25% session with fatigue 2 completes 50% session with fatigue 4 completes 75% session with fatigue 6 completes 100% session with fatigue 8 completes 100% session with no fatigue 10 completes 100% session and more with no fatigue;

c. Body weight;
d. Daily nutritional profiles;

e. Liver function

Within each group, paired data was analyzed using Dunnett's T-test comparing individual time periods. Between groups, analysis was compared by use of a nonparametric method, the Wilcoxan Signed Rank Test. Standard regression analysis was also performed. A p<0.05 was considered significant.

Results

Figure 1:
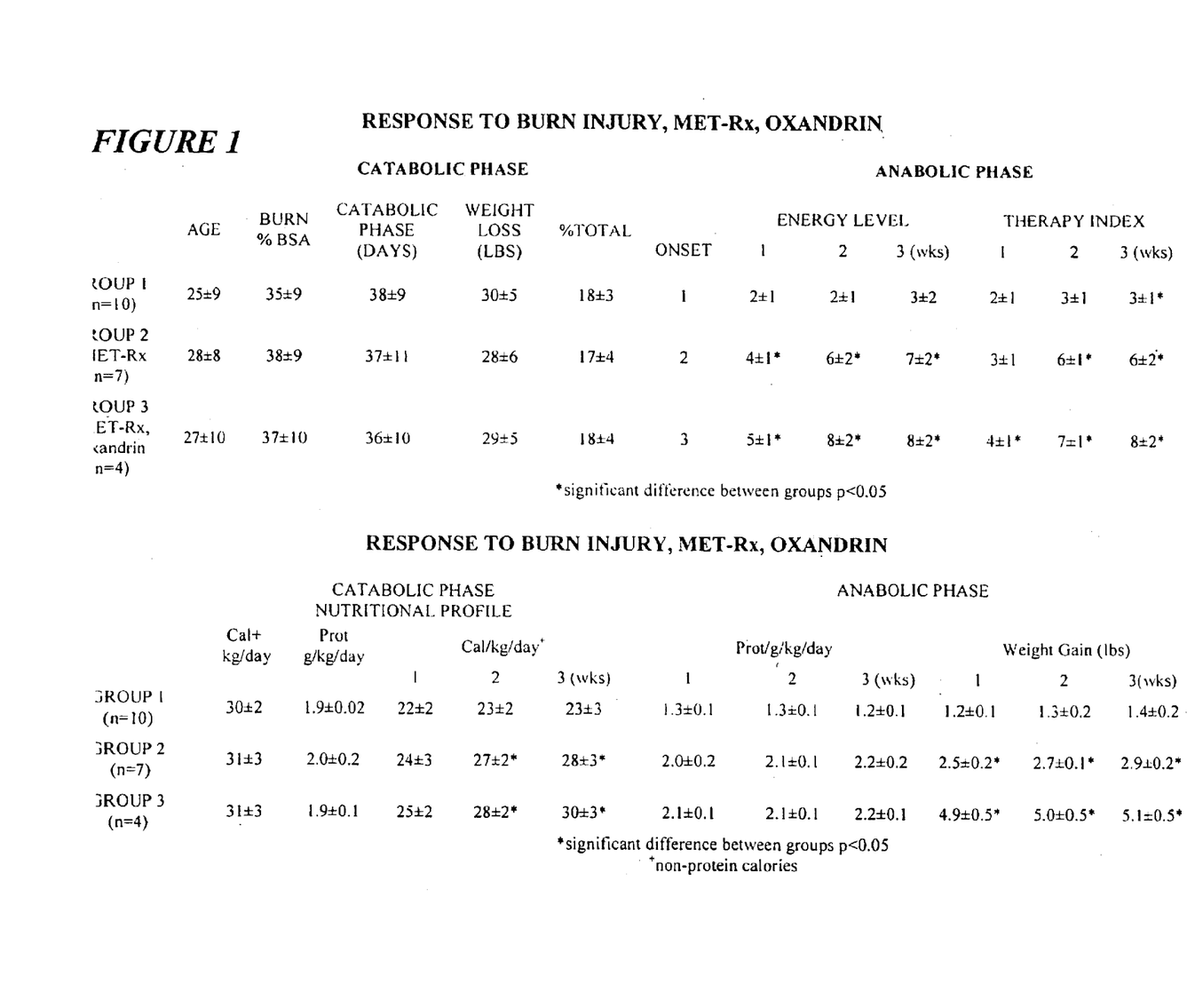
FIG. 1: Effect of oxandrolone and increased protein content on the recovery phase in burn patients (Example 1): measurements of energy level, therapy index and weight gain of burn patients in Groups 1, 2 and 3.
Figure 2:
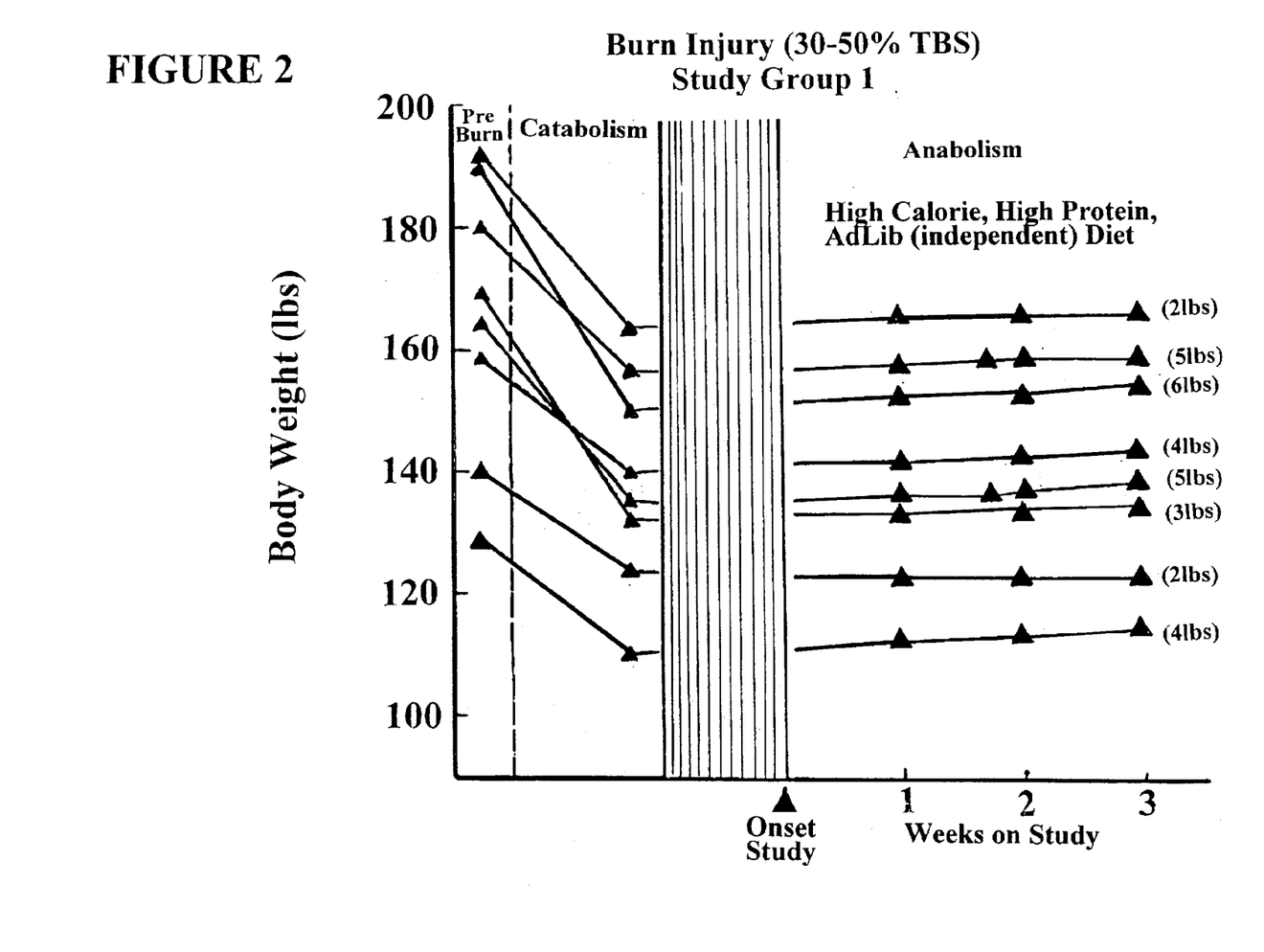
FIG. 2: Body weight of patients (Example 1) with burn injury in Group 1.
Figure 3:
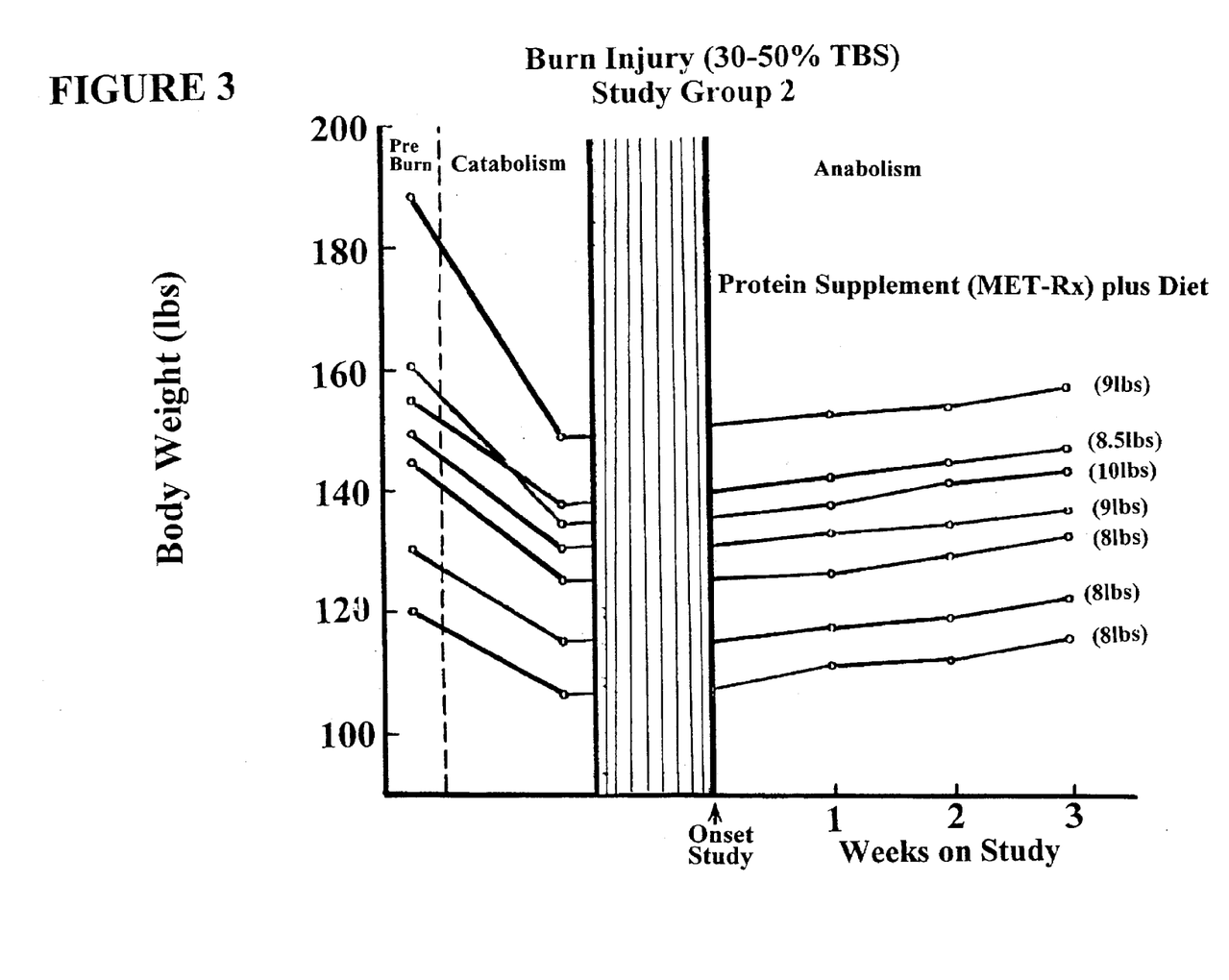
FIG. 3: Body weight of patients (Example 1) with burn injury in Group 2.
Figure 4:
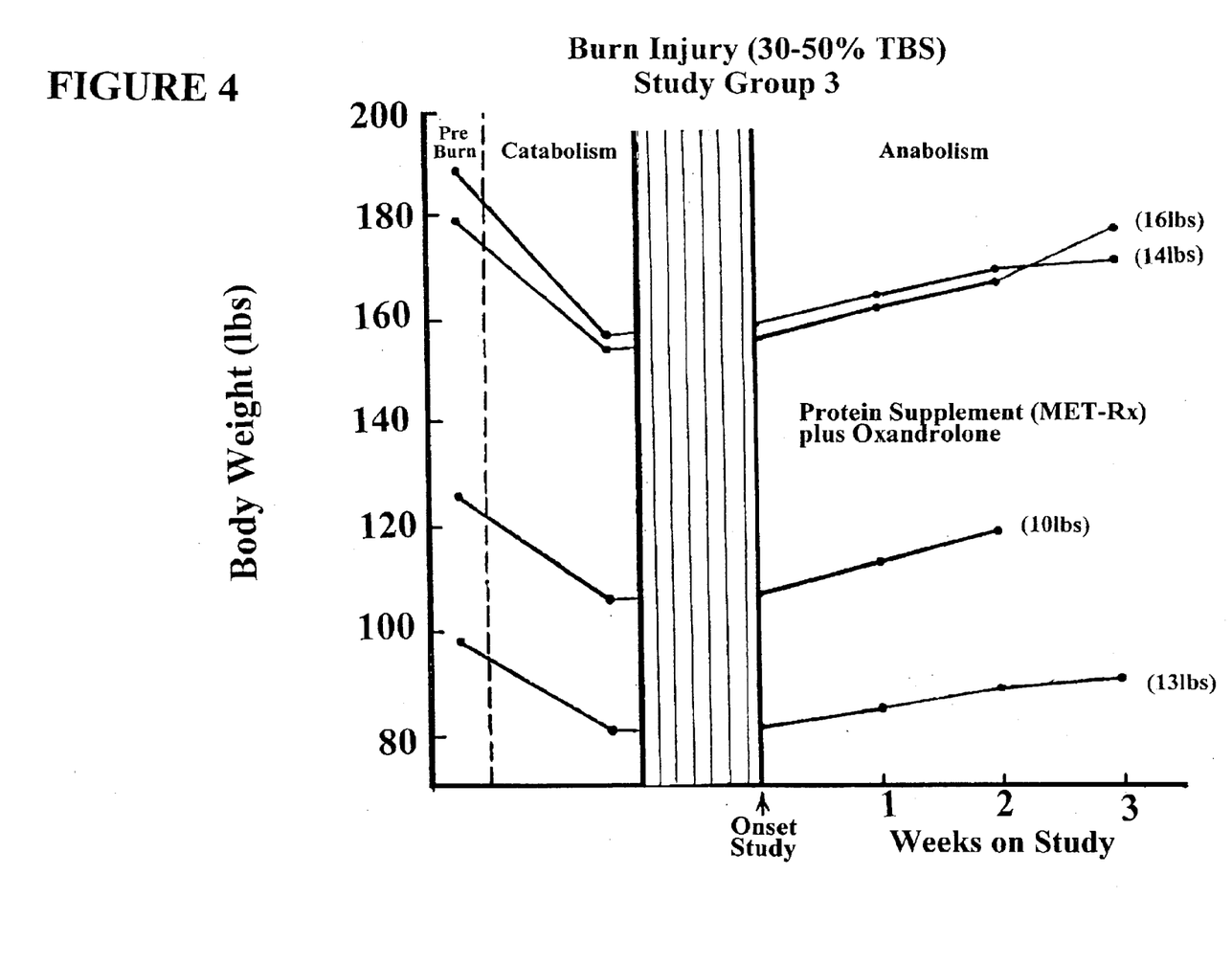
FIG. 4: Body weight of patients (Example 1) with burn injury in Group 3.
Figure 5:
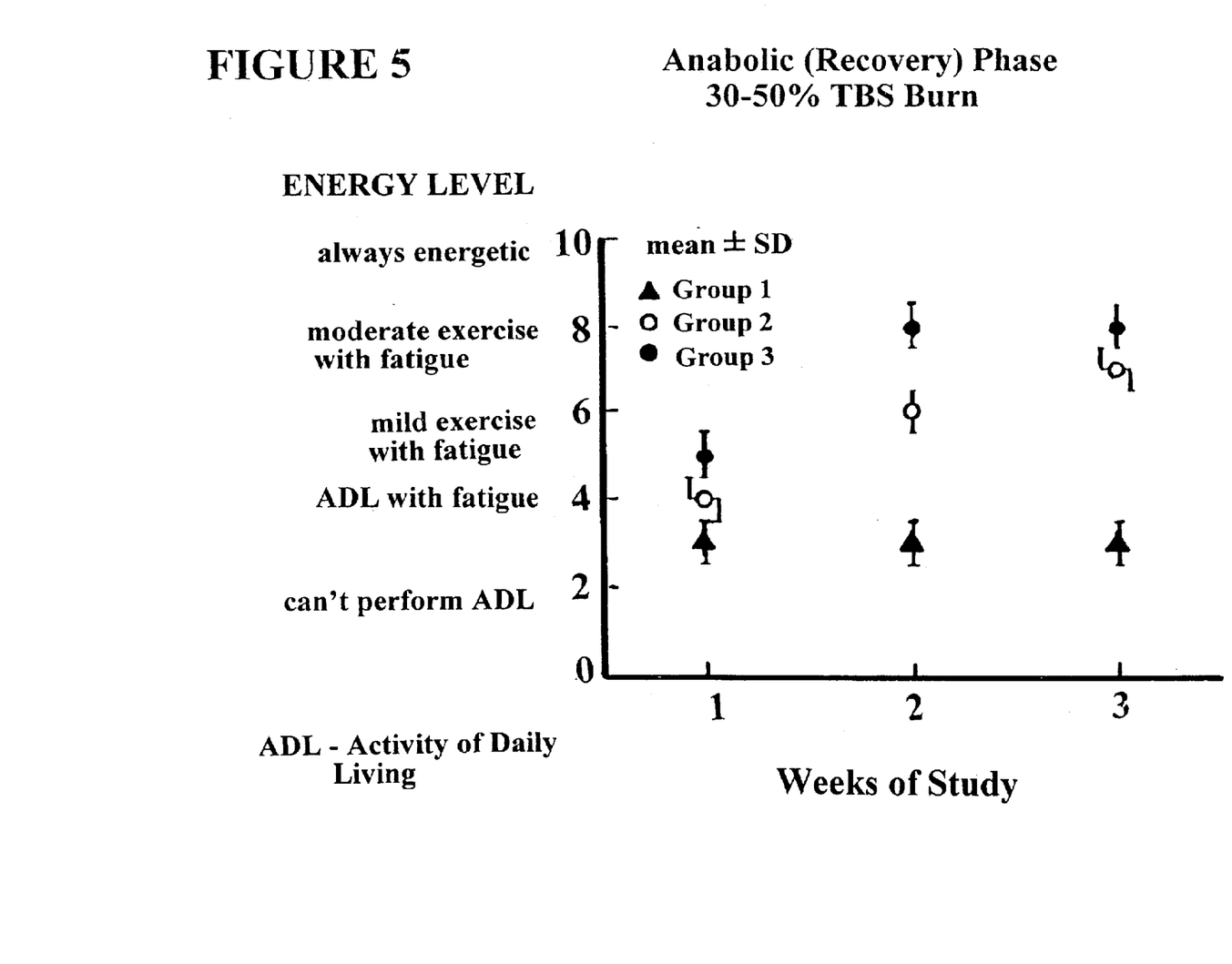
FIG. 5: Energy level (0–10) of burn patients (Example 1) in Groups 1, 2 and 3.
Figure 6:
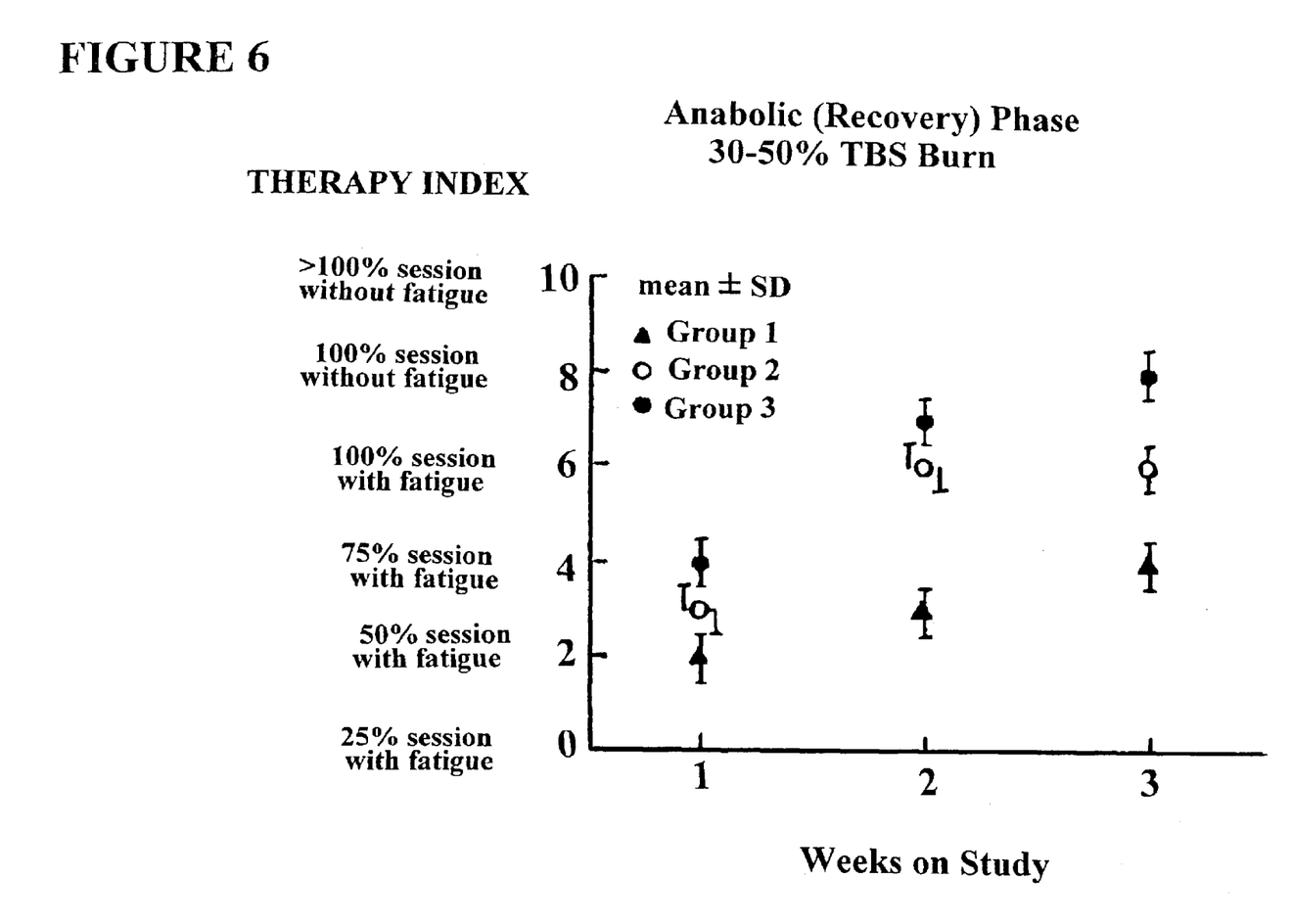
FIG. 6: Therapy index (0–10) of burn patients (Example 1) in Groups 1, 2 and 3.
Figure 7:
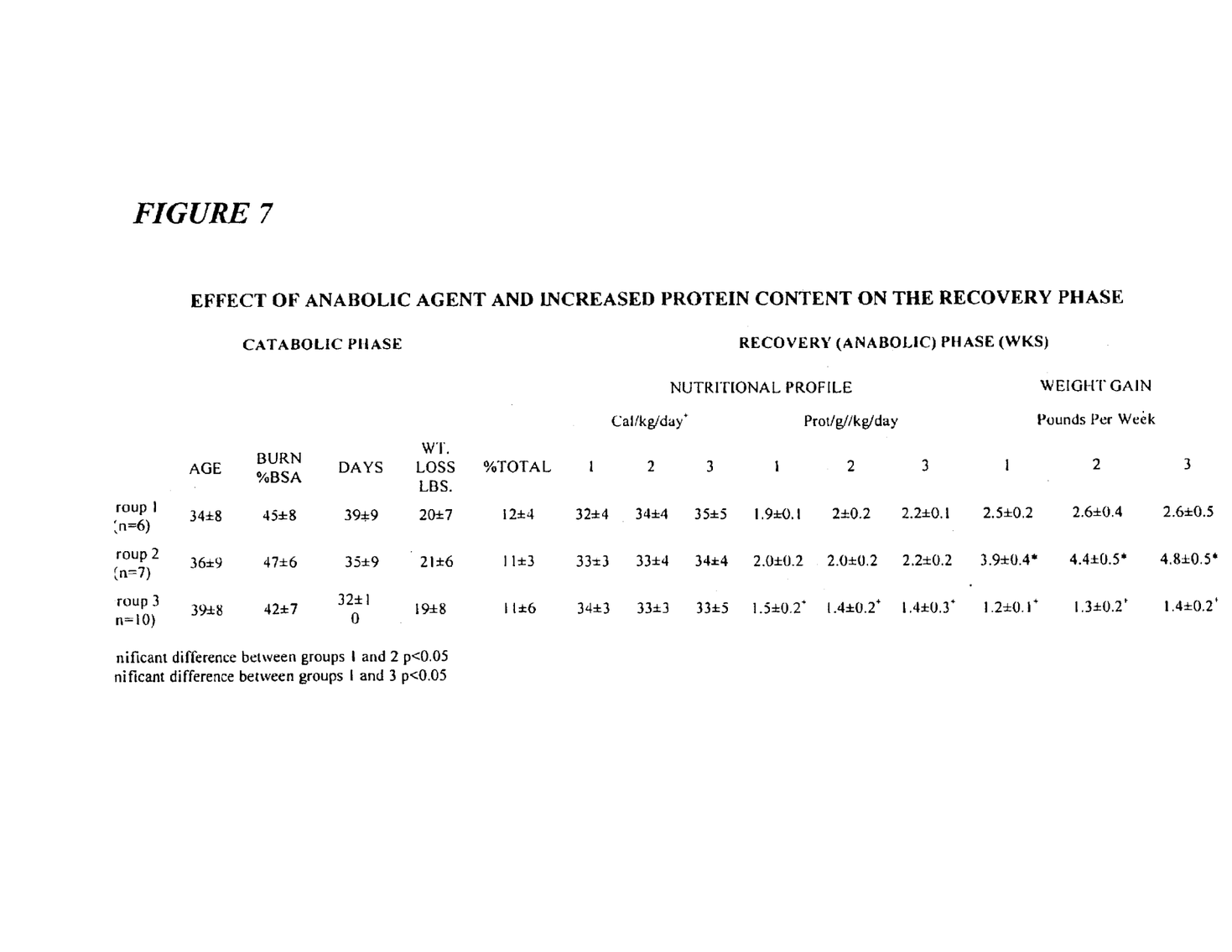
FIG. 7: Effect of oxandrolone and increased protein content on the recovery phase in burn patients (Example 2): measurements of weight gain in Groups 1, 2 and 3.
Figure 8:
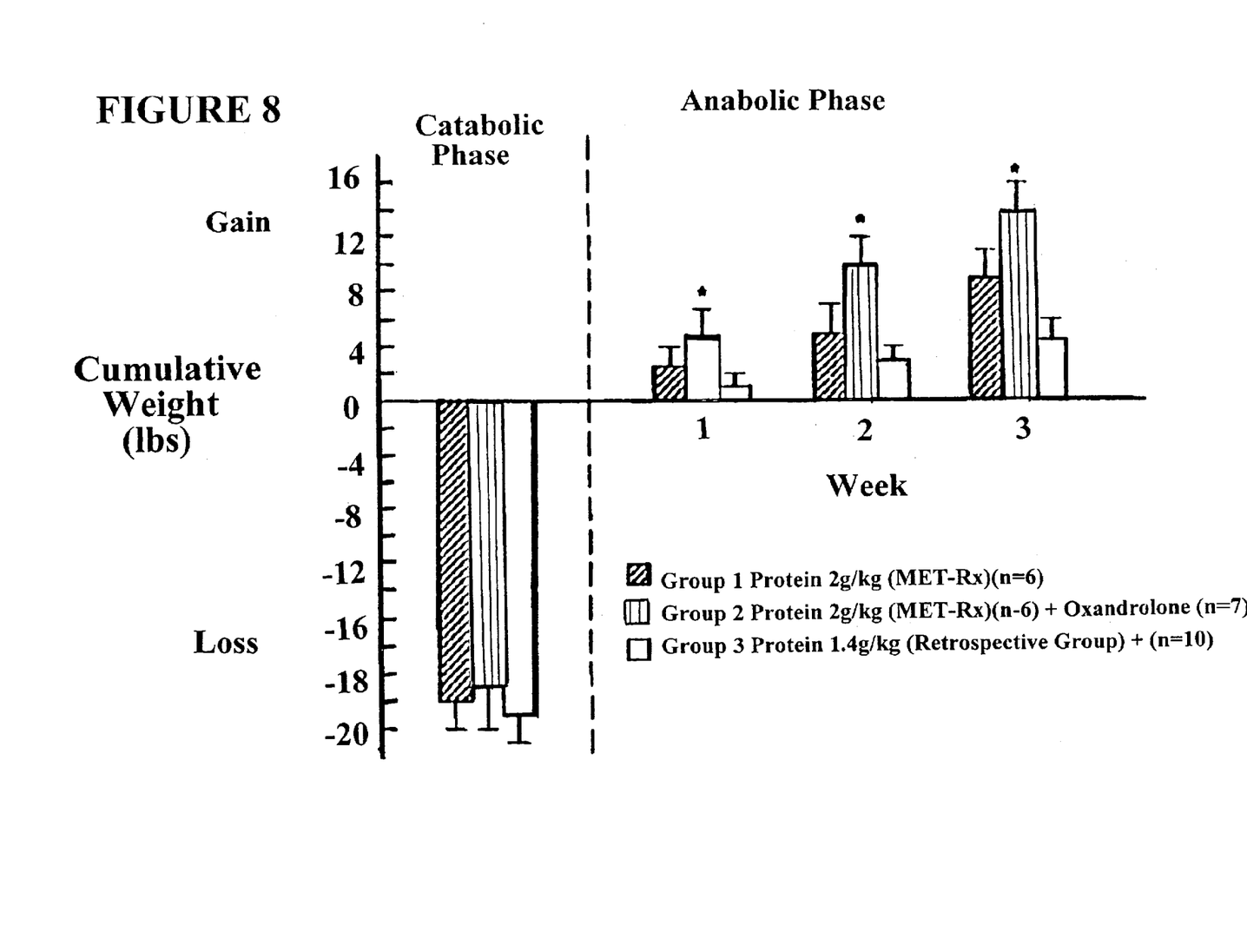
FIG. 8: Body weight of patients (Example 2) with burn injury in Groups 1, 2 and 3.
Figure 9:
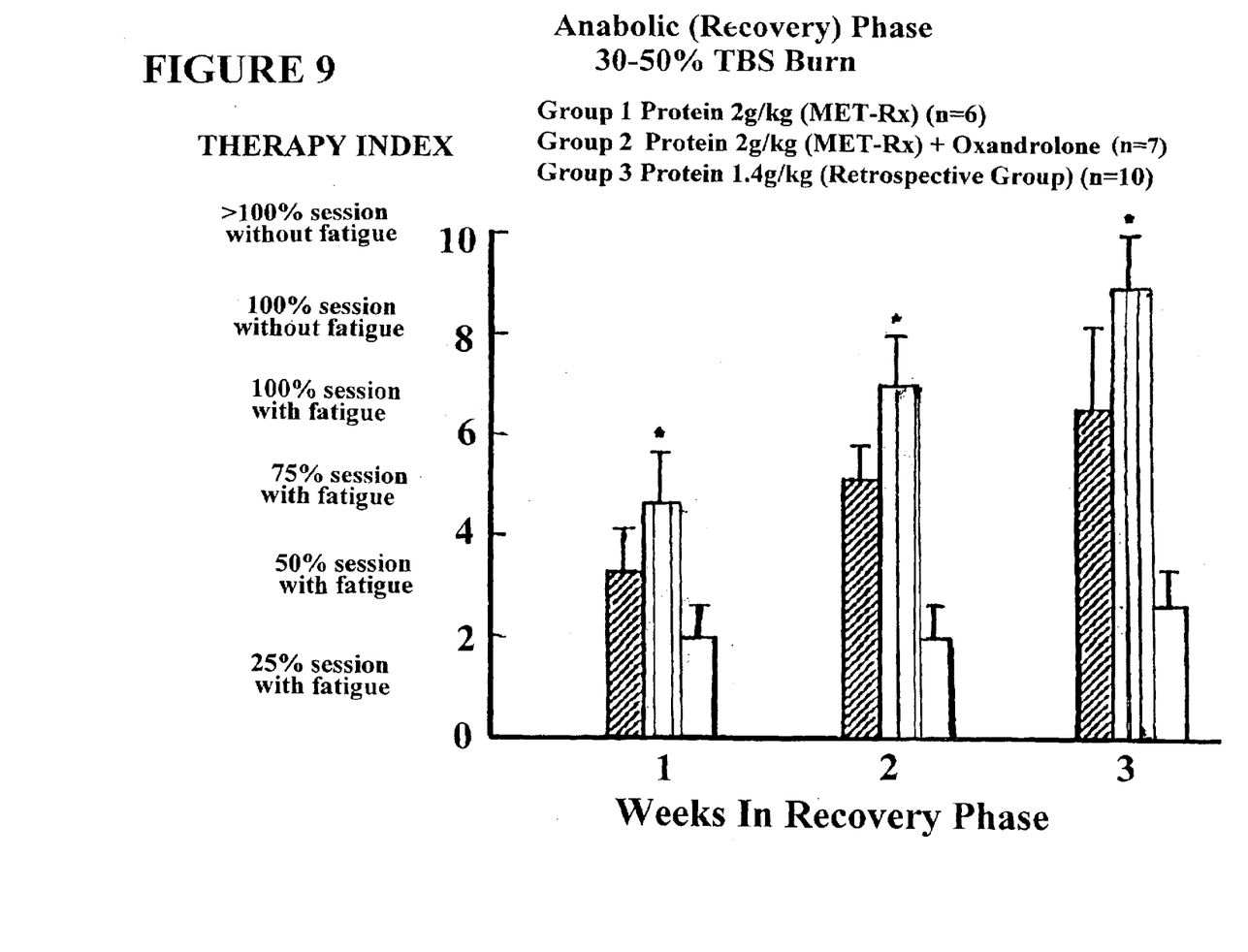
FIG. 9: Therapy index (0–10) of burn patients (Example 2) in Groups 1, 2 and 3.

The results are shown in FIGS. 7–9 and are described below:

All patients survived and have since been discharged to home. Groups 1 and 2 were evenly matched as to age, size of injury, period in the catabolic phase and weight loss. Group 1 had six patients, four males and two females. Group 2 had seven patients, four males and three females. Three patients in each group had a significant inhalation injury requiring initial ventilatory support in excess of two weeks. Weight loss in these patients did not exceed that for the group as a whole. Weight loss averaged 10–12% of reported pre-burn weight in both Group 1 and 2. An unknown portion of the weight loss was likely due to loss of tissue from wound excision as all patients had at least four excisions and graftings, 50% of procedures being excisions to fascia. Once the transition to the recovery phase was defined, no patient developed a significant infection or other acute process which would re-initiate the stress response.

Nutritional Profile

Mean data±standard deviation is shown in FIG. 7. Caloric intake was almost identical between all groups. Compliance with the supplement (MET-Rx) was>90% as the product flavor and texture could be adjusted depending on patient preference. Protein intake was identical in both Groups 1 and 2 being 2.0–2.2 g/kg/day as designed, compared to retrospective Group 3 who were given a high calorie, protein diet with standard supplements with a protein content which equalled 1.3–1.4 g/kg.

Liver Function Tests

One patient in both groups had a transient increase in alkaline phosphatase which resolved spontaneously.

Weight Gain

There was 2.5 to 3 pound weight gain in Group 1 per week, consistently over the three week study period (FIG. 8). In Group 2 weight gain over the three week period was double that of Group 1, a statistically significant difference. Weight gain was significantly increased in both Groups 1 and 2 over the retrospective Group 3.

Physical Therapy Index

In Group 1, the therapy index, a measure of muscle strength and endurance, increased rapidly and most patients were able to compete the entire expected program by the three week period without fatigue (FIG. 9). In Group 2, performance exceeded expectations, especially by week three. Expectations were in large part based on the standard gains in severe burns of this size in the early recovery phase previously managed. Both Groups 1 and 2 showed a significant increase in function over Group 3 at weeks two and three with Group 2 being significantly higher than either of the other groups.

Discharge Time

Average time of discharge from the rehabilitation or recovery phase to home for Group 1 was 26±5 days and Group 2 was 22±4 days while in Group 3 length of stay was 35±7 days. The average patient length of stay in the burn center was 25 days indicating the rapid wound closure and transfer to the rehabilitation center.

Summary

A doubling of weight gain was noted in Group 1 using the protein hydrolysate MET-Rx for the same calorie intake compared to retrospective Group 3 and a marked improvement in muscle function. The biologic value of the added protein is reported to be greater than 95% by the manufacturer (MET-Rx, US, Inc., Irvine Calif.). This value indicates the percent of nitrogen in the hydrolysate retained by the body. Most available supplements use casein as the major protein. Casein has a biologic value of 60–70%. The addition of approximately 74 more grams of protein a day would not explain this doubling of weight unless all the added protein was used for muscle synthesis, a response only expected with an added anabolic stimulus. However, recent data on protein hydrolysate would indicate that biologic properties of a protein hydrolysate exceed that of the contained nitrogen and that bioactive peptides produced by hydrolysis are absorbed intact and can increase anabolism and wound healing. Most of these peptides remain uncharacterized. If all the protein were converted to fat, this would result in only one half a pound of weight gain a week. Therefore, most of the 2.5 pound weight gain would need to be fat free or lean tissue. Correlation with increased strength also indicates the weight to be mostly muscle.

The addition of oxandrolone to the increased protein intake resulted in a marked increase in weight nearly four times that of retrospective Group 3 which at the time were ideally nutritionally managed. Rate of restoration of muscle function was also significantly increased in the oxandrolone group over protein alone. This rate of weight gain is likely muscle mass as opposed to fat since non-protein calorie intake was the same for both Groups 1 and 3. In addition, strength increased and discharge time decreased although the latter may not be a sensitive indication. Anabolic agents are known to markedly increase the efficiency of protein synthesis especially in muscle. Since one pound of muscle is 100 grams of protein and the rest is water, muscle weight gains can occur rapidly when the efficiency of anabolism is accentuated. Weight gain due to water retention is feasible, however water retention is not reported to occur with oxandrolone in doses below 80 mg.

In addition, 3 of 6 patients were followed for eight weeks after discontinuation of three weeks of oxandrolone and the weight remained. No hirsutism has been seen in the three women in the group and a transient small increase in alkaline phosphatase in one patient was the only chemical abnormality noted. This patient also had gallstones and the role of oxandrolone is questionable. Since the gain of muscle over and above normal body composition by body builders using anabolic agents diminishes with discontinuation of the drug the finding of maintenance of weight is important.

In summary, the rate of weight gain and muscle function can be significantly increased in the recovery phase after major burn using the anabolic steroid oxandrolone in combination with a high protein intake including a protein hydrolysate. This data indicates that manipulation of the recovery phase to shorten disability time is very feasible and that endogenous anabolic activity can be markedly increased.

EXAMPLE 3

Oxandrolone Treatment of Patients Suffering from Pressure Sores.

A paraplegic patient was suffering from pressure sores (decubitus ulcers) which had been unhealed for over one year. This patient was treated with oxandrolone (20 mg per day orally) and the sores began to heal. This preliminary result demonstrates that oxandrolone treatment promoted wound healing in decubitus ulcers of long duration. Further experiments using oxandrolone for treatment of pressure sores and other wounds are planned.

References

1. Herndon et al., Treatment of Burns, Curr. Probl. Surg., 1987, Volume 2, pp. 347–373.
2. Wolfe R. R., Nutrition and metabolism in burns, In Chernow B. and Shoemaker W. C., eds., Critical Care, State of the Art, Fullerton, Calif., Society of Critical Care Medicine, 1986, Volume 7, pp. 19–61.
3. Ziegler T., In New Horizons-Frontiers in Critical Care Nutrition, SMMC Fullerton Calif., 1994, p. 244–256.
4. Fox et al. (1962), J. Clin. Endocrinol. Metab. 22: 921–924.
5. Karim et al. (1973), Clin. Pharmacol. Therap. 14: 862–869.
6. Masse et al. (1989), Biomedical and Environmental Mass Spectrometry 18:429–438.
7. Mendenhall et al. (1993), Hematology 17(4): 564–576.
8. Bonkovsky et al. (1991), The American Journal of Gastroenterology 86(9): 1209–1218.

What is claimed is:

1. A method of increasing the rate of healing of a skin wound in a patient suffering from a skin wound which comprises administering a therapeutically effective amount of oxandrolone to the patient.

2. A method according to claim 1 wherein the skin wound is an ulcer.

3. A method according to claim 2 wherein the ulcer is a decubitus ulcer or a diabetic ulcer.

4. A method according to claim 1 wherein the skin wound comprises a skin graft.

5. A method according to claim 1 wherein the skin wound is a burn.

6. A method according to claim 1 wherein the amount of oxandrolone is about 1–100 mg per day.

7. A method according to claim 6 wherein the amount of oxandrolone is about 80 mg per day.

8. A method according to claim 6 wherein the amount of oxandrolone is about 20 mg per day.

9. A method according to claim 6 wherein the amount of oxandrolone is about 10 mg per day.

10. A method according to claim 6 wherein the amount of oxandrolone is about 2.5 mg per day.

11. A method according to claim 1 wherein the oxandrolone is administered orally.

12. A method according to claim 1 wherein the oxandrolone is administered topically.

13. A method according to claim 1 wherein the oxandrolone is administered by injection.

14. A method according to claim 1 wherein the oxandrolone is in a solid dosage form.

15. A method according to claim 1 wherein the oxandrolone is in a liquid dosage form.

16. A method according to claim 1 wherein the oxandrolone is in a sustained-release formulation.

17. A method according to claim 1 wherein the oxandrolone is 17α-methyl-17β-hydroxy-2-oxa-5α-androstan-3-one.

18. A method of increasing the rate of weight gain during the recovery phase after burn-induced weight loss in a patient having a burn wound which comprises administering a therapeutically effective amount of oxandrolone to the patient.

19. A method according to claim 18 wherein the amount of oxandrolone is about 1–100 mg per day.

20. A method according to claim 19 wherein the amount of oxandrolone is about 80 mg per day.

21. A method according to claim 19 wherein the amount of oxandrolone is about 20 mg per day.

22. A method according to claim 19 wherein the amount of oxandrolone is about 10 mg per day.

23. A method according to claim 19 wherein the amount of oxandrolone is about 2.5 mg per day.

24. A method according to claim 18 wherein the oxandrolone is administered orally.

25. A method according to claim 18 wherein the oxandrolone is administered topically.

26. A method according to claim 18 wherein the oxandrolone is administered by injection.

27. A method according to claim 18 wherein the oxandrolone is in a solid dosage form.

28. A method according to claim 18 wherein the oxandrolone is in a liquid dosage form.

29. A method according to claim 18 wherein the oxandrolone is in a sustained-release formulation.

30. A method according to claim 18 wherein the oxandrolone is 17α-methyl-17β-hydroxy-2-oxa-5α-androstan-3-one.

31. A method according to claim 18 further comprising administering a protein supplement.

32. A method according to claim 18 wherein the weight comprises lean body mass.

33. A method according to claim 18 wherein the weight gained is maintained.

* * * * *